United States Patent [19]

Nishibori et al.

[11] Patent Number: 5,710,309
[45] Date of Patent: Jan. 20, 1998

[54] PROCESS FOR PRODUCING TRIS (TRIBROMONEOPENTYL) PHOSPHATE

[75] Inventors: Setsuo Nishibori; Hideaki Ohnishi, both of Shiga, Japan

[73] Assignee: Dai-Ichi Kogyo Seiyaku Co., Ltd., Kyoto, Japan

[21] Appl. No.: 657,840

[22] Filed: May 31, 1996

[30] Foreign Application Priority Data

Jun. 8, 1995 [JP] Japan ................... 7-142142

[51] Int. Cl.$^6$ .................................................. C07F 9/09
[52] U.S. Cl. .................................... 558/102; 558/203
[58] Field of Search ............................. 558/102

[56] References Cited

U.S. PATENT DOCUMENTS 4,714,771  12/1987  Liu .......................... 558/102

FOREIGN PATENT DOCUMENTS

| 45-36894 | 11/1970 | Japan . |
| 46-6865 | 2/1971 | Japan . |
| 62-187478 | 8/1987 | Japan . |
| 3-193793 | 8/1991 | Japan . |

*Primary Examiner*—Michael G. Ambrose
*Attorney, Agent, or Firm*—Jordan and Hamburg

[57] ABSTRACT

The invention relates to a process for producing tris (tribromoneopentyl) phosphate (TTBNPP), which is of value as a flame retardant. The process comprises reacting tribromoneopentyl alcohol with a phosphorus oxyhalide in the presence of anhydrous aluminum chloride as catalyst in an organic solvent to give tris(tribromoneopentyl) phosphate characterized in that a basic magnesium salt is added to the reaction mixture at the completion of the reaction. Compared with the conventional production technology, the process of the invention is conducive to high production safety and insures a high yield and a high recovery rate through a simplified procedure.

4 Claims, No Drawings

5,710,309

PROCESS FOR PRODUCING TRIS (TRIBROMONEOPENTYL) PHOSPHATE

FIELD OF THE INVENTION

The present invention relates to a process for producing tris(tribromoneopentyl) phosphate (hereinafter sometimes referred to briefly as TTBNPP) which is of value as a flame retardant.

BACKGROUND OF THE INVENTION

As disclosed in JP-B-45036894 and JP-B-46006865, TTBNPP is a very useful flame retardant for flammable high molecular organic polymers, which is possessed of high flame retardancy, heat stability, resistance to hydrolysis, and light stability.

TTBNPP is generally synthesized by subjecting 3 mols of tribromoneopentyl alcohol and 1 mol of a phosphorus oxyhalide to dehydrohalogenation reaction.

According to JP-B-45036894, this compound can be produced by reacting tribromoneopentyl alcohol with a phosphorus oxyhalide, e.g. phosphorus oxychloride, in the presence of a dehydrohalogenating agent such as pyridine in an inert organic solvent. In connection with this process, which involves the use of an expensive dehydrohalogenating agent, it might be contemplated to recover this reagent by providing a recovery step but such a system would not be economically favorable because recovery rate is not high while the process become complicated.

JP-B-46006865 describes a production process which comprises subjecting tribromoneopentyl alcohol and phosphorus oxychloride to dehydrohalogenation reaction using anhydrous aluminum chloride as a catalyst and, after cooling, recrystallizing the resulting solid reaction product using benzene or chlorobenzene. In this process, however, in order to remove the catalyst, anhydrous aluminum chloride and residual acidic byproducts such as hydrogen chloride, thoroughly from the reaction mixture, it is necessary to employ an organic solvent in a large quantity or repeat recrystallization several times, thus making the process economically unfavorable. If said acidic substances remain, equipment corrosion would occur in the subsequent filtration and drying stages and in the use of the product as a flame retardant, they can be a cause of equipment corrosion and present work safety problems.

To cope with these problems, JP-A-62187478 proposes a process which comprises carrying out the reaction in an inert solvent such as ethylene tetrachloride and, for elimination of the catalyst, washing a slurry of crystals with hydrochloric acid or the like. However, this technology is not only complicated but also requires several cycles of rinsing for removal of hydrochloric acid, which produce an enormous amount of waste rinse water.

On the other hand, JP-A-03193793 discloses a technology claimed to be conducive to improved production efficiency per unit reactor capacity which comprises conducting the reaction in a high-boiling solvent such as dichlorobenzene, contacting the resulting reaction mixture with water or a neutral, basic or acidic aqueous medium at a temperature not causing precipitation of crystalline TTBNPP, and finally cooling the product to provide crystals. However, because water must be added under the condition not causing precipitation of TTBNPP, the addition temperature is restricted. Thus, the temperature must not be over the boiling point of water or the azeotropic point of the organic solvent-water system used. Moreover, there is a risk of bumping due to the heat of crystallization which is evolved in the precipitation of TTBNPP. To avoid this trouble, water must be added at a sufficiently low temperature with respect to the boiling point but since the concentration of TTBNPP in the system is high, the reaction mixture as a whole tends to be solidified all at once upon being supercooled. Therefore, the organic solvent that can be used is limited to those solvents which are high-boiling and in which TTBNPP is readily soluble, such as dichlorobenzene. On the other hand, if a neutral or acidic aqueous medium is added, there is encountered the same problem as that mentioned with regard to acidic substances in the processes according to JP-B-46006865 and JP-A-62187478. On the other hand, when a basic aqueous medium such as an aqueous solution of sodium carbonate is added and if the strong base sodium carbonate is allowed to remain in the product, there is the risk of the phosphate group or tribromoneopentyl group being decomposed on heating in the drying step as well as the safety problem in product handling. Therefore, it is necessary to neutralize the slurry or carry out sufficient rinsing. As pointed out above, the conventional TTBNPP production technologies are not satisfactory enough for commercial exploitation in the aspects of safety, productivity, and product quality.

DISCLOSURE OF THE INVENTION

The present invention has for its object to provide a commercial TTBNPP production process which would overcome the drawback of the prior art failing to concurrently meet the requirements of enhanced productivity and satisfactory product quality, which process consists in a simplified procedure with enhanced safety and high production efficiency and without compromise in quality.

In view of the above state of the art the inventors of the present invention did much research for the purpose of establishing a method of harvesting TTBNPP crystals of high quality from the reaction mixture obtained by reacting tribromoneopentyl alcohol with a phosphorus oxyhalide in the presence of the catalyst anhydrous aluminum chloride in an organic solvent and discovered that mere addition of a basic magnesium salt results not only in simplification of the process while assuring high safety and high production efficiency but also in improved quality of the product TTBNPP. The present invention has been developed on the basis of the above finding.

The present invention is essentially directed to a process for producing TTBNPP which comprises reacting tribromoneopentyl alcohol with a phosphorus oxyhalide using anhydrous aluminum chloride as a catalyst in an organic solvent and, after completion of the reaction, adding a basic magnesium salt to the reaction mixture.

Since the basic magnesium salt is added to the reaction mixture under anhydrous conditions in the process of the invention, the basic substance can be added without eliciting a steam explosion even when the reaction temperature is over 100° C. Moreover, even when the solubility of TTBNPP in the reaction solvent reaches the saturation point at a temperature up to 100° C., the basic magnesium salt provides crystal nuclei so that a highly concentrated Slurry can be obtained without the trouble of crystal deposits on the vessel wall or omnibus solidification of the reaction mixture, the charge of TTBNPP per unit reactor capacity can be increased, and the transportation of the slurry and other workability parameters can be improved. At the same time, even when an organic solvent providing an azeotropic mixture with water and giving an azeotropic point not higher than 100° C. is employed, the slurry can be cooled to less than the azeotropic point and, then, water for promoting neutralization of aluminum chloride and residual hydrogen halide can be safely added. Moreover, because the solubility of the basic magnesium salt in water is low and the aqueous solution is, therefore, weakly alkaline at pH about 10–11, pH adjustment need not be made even if a stoichiometric excess of the salt is added with respect to the acidic substances unlike the case in which the hydroxide or carbonate of sodium, potassium, calcium, barium or the like is added. Therefore, the process of the invention is a commercially very useful process.

The process of the invention is now described in detail.

As already known, TTBNPP can be produced by the following reaction. Preferably 2.8–3.2 molar equivalents of tribromoneopentyl alcohol is reacted with each mol of a phosphorus oxyhalide. If the proportion of the alcohol is less than 2.8 mols, the yield of the tris-phosphate will be damaged by the formation of the mono-phosphate and bis-phosphate. On the other hand, the use of tribromoneopentyl alcohol in a proportion of more than 3.2 mols will not contribute to the yield of the tris-phosphate but the excess of the alcohol will simply become a waste.

In terms of availability and cost, the phosphorus oxyhalide is preferably phosphorus oxychloride.

As the catalyst, anhydrous aluminum chloride is most suitable from the standpoint of catalytic activity and cost. The proper level of addition of the catalyst is 0.05–0.5 weight % with respect to the theoretical yield of TTBNPP. If the level of addition is less than 0.05 weight %, the reaction rate will be drastically reduced to prolong the reaction time. The use of the catalyst in a proportion of more than 0.5 weight % will not shorten the reaction time but rather increase the subsequent separation or neutralization load to detract from the economics of the process.

As the organic solvent for the reaction, those solvents which are inert to tribromoneopentyl alcohol, phosphorus oxychloride, anhydrous aluminum chloride and hydrogen chloride and substantially insoluble in water can be employed. Moreover, from the productivity point of view, the solvents in which TTBNPP is highly soluble in the neighborhood of the boiling point are preferred. Thus, benzene, toluene, xylene, ethylbenzene, chlorobenzene, dichlorobenzene, tetrachloroethane, tetrachloroethylene, and trichloroethane can be mentioned by way of example. The amount of the solvent should be large enough to thoroughly dissolve TTBNPP at the temperature prevailing at completion of the reaction and yet as small as possible from the standpoint of productivity.

A reaction rate of not less than 95% can be achieved by adding phosphorus oxychloride dropwise to a solution containing tribromoneopentyl alcohol and anhydrous aluminum chloride in an organic solvent at a temperature of 80°–100° C. and stirring the mixture further at a temperature up to the boiling point of the organic solvent.

In the process of the present invention, a basic magnesium salt is added to the resulting reaction mixture.

The basic magnesium salt that is used in the practice of the present invention is at least one member selected from the group consisting of magnesium oxide, magnesium hydroxide, magnesium carbonate, magnesium carbonate-magnesium hydroxide, and the corresponding hydrates and is preferably in the form of a powder. Moreover, for improved water resistance or dispersibility in the substrate resin, the powder coated with, for example, an organic coating material can also be used with success.

The addition temperature may range from the temperature prevailing at completion of the reaction to the boiling point of the organic solvent or a temperature established by cooling the reaction system and not causing precipitation of crystals. Regarding the method of addition, the salt powder can be directly added or in the form of a slurry prepared using the same organic solvent as the reaction solvent or an organic solvent having a boiling point over the addition temperature. However, when a slurry prepared using an organic solvent is added, the temperature of the reaction mixture is lowered with the result that crystallization would begin in the course of addition but this will not interfere with the production.

The preferred level of addition is 0.01–10 weight % with respect to the theoretical yield of TTBNPP. Any proportion of less than 0.01 weight % will not be sufficient to neutralize the system so that the pH will have to be adjusted after addition of water and in cases where crystals separate out at the temperature at which water can be safely added, the effect of the salt as crystal nuclei will not sufficiently develop with the result that crystals tend to be deposited on the vessel wall. The use of the salt in a proportion of more than 10 weight % will not be rewarded with an additional effect as far as production is concerned. Moreover, magnesium oxide, magnesium hydroxide, or magnesium carbonate has heretofore been used broadly as a flame retardant, a reinforcing agent and/or a stabilizer for resins and rubber, and their residues in TTBNPP which is to be used as a flame retardant are tolerable insofar as their concentrations are reasonably low but an excessive concentration of the salt in the final product might detract from the physical properties of the resin to which it is added so that the universality of the product TTBNPP as a flame retardant is decreased.

The basic magnesium salt added to the reaction mixture acts as crystal nuclei. Even when the concentration of TTBNPP in the reaction mixture is high, a stable slurry of crystals can be obtained without troubles such as abrupt omnibus precipitation from a supercooled system or deposition of crystals on the reactor wall. Whereas bumping occurs due to the heat of crystallization when the organic solvent oversaturated with TTBNPP is brought into contact with water at a temperature near 100° C., the process of the invention is safe because the mixture can be cooled in stable condition down to a sufficiently low temperature where contact with water does not cause bumping. Moreover, it becomes possible to employ a solvent in which TTBNPP is not so highly soluble at a temperature around 90° C. and even if a solvent having a boiling point which would not be burdensome in the drying stage of about 90°–150° C., production with a high efficiency can be insured.

Furthermore, in the present invention, the catalyst aluminum chloride and residual hydrogen chloride can be completely neutralized either by adding water to the organic solvent slurry or pouring the slurry in water. The amount and temperature of water, agitation and other conditions for neutralization are not so critical but because the system to be neutralized is a heterogenous three-phase system consisting of solid TTBNPP, organic solvent, and water, the amount of water is preferably not less than 1 weight % with respect to the theoretical yield of TTBNPP in order that thorough neutralization may be achieved and it is also preferable to stir the whole system well at a temperature below the boiling point of the system. If neutralization is incomplete, volatile acidic substances may remain in the product.

The basic magnesium salt for use in the present invention gives a basic aqueous slurry showing a pH value somewhere between about 10 and about 11 and its solubility in water is low. Thus, when neutralization is carried out with a strong base such as sodium hydroxide, potassium hydroxide, calcium hydroxide, sodium carbonate or potassium carbonate, it is essential to adjust the pH of the system because the tribromo moiety or phosphate group is otherwise hydrolyzed to detract from the product yield or the strong base remains in the product to jeopardize working safety. In contrast, the present invention provides a simplified process because even if pH adjustment is omitted, there is no risk for degradation of the product or deterioration of working safety.

If necessary, the magnesium halide formed on neutralization can be removed from the product by washing with water or a solvent that will dissolve water, halogen salt and the organic solvent used as the reaction solvent, such as a lower alcohol.

The completely neutralized slurry is then cooled to precipitate TTBNPP. The recovery rate of TTBNPP can be improved by adding a poor solvent for TTBNPP which is soluble in the reaction organic solvent, such as cyclohexane, hexane, heptane, or the like to the slurry in this crystallization stage.

The TTBNPP slurry thus prepared is subjected to solid-liquid separation using a centrifuge, a decanter, a suction filter or the like, then washed with water and/or an organic solvent where necessary, and dried in a routine powder production flow. Through this flow, a crystalline powder of high quality TTBNPP can be recovered in good yield. In the above-described process of the present invention, high-quality TTBNPP can be produced by a safe, simple procedure. As the resulting high-quality TTBNPP free of volatile acidic matter is added to a flammable high molecular organic polymer, there is provided a flame-retardant organic polymer which would not cause metal mold or die corrosion or undergo discoloration due to thermal aging.

DETAILED DESCRIPTION OF THE PREFERRED EMBODIMENTS

The following examples are intended to describe the present invention in further detail and should by no means be construed as defining the scope of the invention. In the respective examples, all parts and percents are by weight.

EXAMPLE 1

A one-liter flask equipped with a stirrer, condenser, thermometer, and nitrogen inlet was charged with 488 g (1.5 mols) of tribromoneopentyl alcohol (manufactured by Bromine Chemical Ltd., purity 98%), 1.0 g of anhydrous aluminum chloride, and 500 g of chlorobenzene and the charge was heated to 100° C. under nitrogen gas. With this temperature maintained, 76.7 g (0.5 mol) of phosphorus oxychloride was added dropwise over 30 minutes and after completion of dropwise addition, the mixture was stirred at the same temperature for another 30 minutes. Thereafter, the temperature was increased to 120° C. over one hour and the reaction mixture was stirred for a further 5 hours. The reaction rate for TTBNPP at this point of time was 97.2%. At this temperature, 2.6 g of magnesium hydroxide (Kysma 5A, manufactured by Kyowa Chemical Industry Co., Ltd.), corresponding to 0.5% of the theoretical yield (510 g) of TTBNPP (calculated on the assumption that the purity of tribromoneopentyl alcohol was 100%), was added. After thorough dispersion of magnesium hydroxide, the reaction mixture was cooled, whereupon crystals began to separate out at 109° C. and the evolution of heat due to the heat of crystallization was observed. Though the system was further cooled to 90° C., no crystal deposits were found on the reactor wall, thermometer or stirrer and a stable slurry was obtained. To this slurry was added 200 g of hot water at 80° C. and the mixture was consistently stirred at 85°–90° C. for 30 minutes, after which it was cooled to 20° C. The resulting slurry could be easily filtered through a filter paper (TOYO NO. 5A, manufactured by Toyo Roshi Co.) using a suction filter. The filter cake was washed with 200 g of chlorobenzene. One-half of the cake was dried at 130° C. for 5 hours to provide 241 g of TTBNPP crystals. Relative to the theoretical yield of TTBNPP, the yield was 94.0% and the recovery rate was 96.7%. The purity determined by GPC (gel permeation chromatography) was 99.9%. See Table 1.

A portion of the filter cake was submitted to a qualitative test for volatile acidic matter. On the other hand, the product obtained time was subjected to the qualitative test for volatile acidic matter and color evaluation at melting and the thermal discloration test.

EXAMPLE 2

To the reaction mixture showing a reaction rate of 97.4% as obtained by using the same reactor, charge and procedure as in Example 1 was added a slurry prepared by dispersing 10.2 g of magnesium carbonate, corresponding to 2% of the theoretical yield (510 g) of TTBNPP, in 100 g of chlorobenzene. The magnesium carbonate became immediately dispersed and the system was promptly cooled, whereupon crystallization began with the evolution of heat at 109° C. The system was further cooled to 95° C., at which temperature 25 g of water was added. The mixture was stirred at 80° C. for one hour, at the end of which time it was cooled to 20° C. The resulting slurry could be easily filtered through a filter paper (TOYO NO. 5A, Toyo Roshi) using a suction filter. The filter cake was washed with 100 g of chlorobenzene. One-half of the filter cake was dried in vacuo at 120° C. to provide 245 g of TTBNPP crystals. Relative to the theoretical yield of TTBNPP, the yield was 94.1% and the recovery rate was 96.6%. The purity determined by GPC was 99.8%. See Table 1.

EXAMPLE 3

The same reactor as the one used in Example 1 was charged with 341 g (1.05 mols) of tribromoneopentyl alcohol, 0.4 g of aluminum chloride, And 600 g of xylene and the charge was heated to 100° C. with introduction of nitrogen gas. With this temperature maintained, 53.7 g (0.35 mol) of phosphorus oxychloride was added dropwise over 30 minutes and after completion of dropwise addition the mixture was stirred at the same temperature for another one hour. Thereafter, the temperature was increased to 130° C. over 1.5 hours and the reaction mixture was stirred for a further 5 hours. The reaction rate for TTBNPP at this point of time was 96.4%. At this temperature, 3.6 g of magnesium hydroxide (Kysma 5A, manufactured by Kyowa Chemical Industries, Ltd.) corresponding to 1% of the theoretical yield (357 g) of TTBNPP was added. After thorough dispersion of magnesium hydroxide, the reaction mixture was cooled, whereupon crystals began to separate out at 120° C. and the evolution of heat due to the heat of crystallization was observed. Even when the system was further cooled to 90° C., no crystal deposits were found on the reactor wall, thermometer or stirrer and a stable slurry was obtained. To this slurry was added 100 g of hot water at 80° C. and the mixture was consistently stirred at 85°–90° C. for 30 minutes, after which it was cooled to 20° C. The resulting slurry could be easily filtered through a filter paper (TOYO NO. 5A, manufactured by Toyo Roshi) using a suction filter. The filter cake was washed with 100 g of xylene. One-half of the filter cake was dried in vacuo at 120° C. to provide 172 g of TTBNPP crystals. Relative to the theoretical yield of TTBNPP, the yield was 95.4% and the recovery rate was 98.9%. The purity determined by GPC was 99.5%. See Table 1.

EXAMPLE 4

The same reactor as the one used in Example 1 was charged with 585 g (1.8 mols) of tribromoneopentyl alcohol, 1.2 g of anhydrous aluminum chloride, and 400 g of chlorobenzene and the charge was heated to 100° C. under nitrogen gas. With this temperature maintained, 92.0 g (0.6 mol) of phosphorus oxychloride was added dropwise over one hour and after completion of dropwise addition the mixture was stirred at the same temperature for another 30 minutes. Thereafter, the temperature was increased to 125° C. over one hour and the reaction mixture was stirred for a further 3 hours. The reaction rate for TTBNPP at this point of time was 97.8%. At this temperature, a slurry prepared by dispersing 30.6 g of magnesium hydroxide (Kysma 5A, manufactured by Kyowa Chemical Industry Co., Ltd.), corresponding to 5% of the theoretical yield (611 g) of TTBNPP, in 50 g of chlorobenzene was added. After thorough dispersion of magnesium hydroxide, the reaction mixture was cooled, whereupon crystals began to separate out at 114° C. and the evolution of heat due to the heat of crystallization was observed. Though the system was further cooled to 80° C., no crystal deposits were found on the reactor wall, thermometer or stirrer and a stable slurry was obtained. To this slurry was added 200 g of hot water of 80° C. and the mixture was consistently stirred at 80° C. for 30 minutes, after which 200 g of cyclohexane was added and the mixture was cooled to 20° C. The resulting slurry could be easily filtered through filter paper (TOYO NO. 5A, manufactured by Toyo Roshi) using a suction filter. The filter cake was washed with 200 g of chlorobenzene. One-half of the cake was dried at 130° C. for 5 hours to provide 313 g of TTBNPP crystals. Relative to the theoretical yield of TTBNPP, the yield was 97.4% and the recovery rate was 99.6%. The purity determined by GPC was 99.6%. See Table 1.

Comparative Example 1

Using the same reactor and charge as those used in Example 1, the reaction was similarly carried out. The reaction rate was 97.3%. Without any addition, the reaction mixture was directly cooled. When the internal temperature had reached 104° C., crystallization en bloc occurred suddenly so that most of the mixture became a non-flowable solid with only a portion close to the stirrer giving a slurry. The solid was taken out from the flask and using about 1,500 g of chlorobenzene based on the theoretical yield 510 g of TTBNPP, recrystallization was carried out in 2 cycles. This slurry of TTBNPP crystals was filtered through filter paper (TOYO NO. 5A, manufactured by Toyo Roshi) using a suction filter and one-half of the filter cake was dried to provide 200 g of TTBNPP. The yield was 78.4% and the recovery rate was 80.6%. The purity determined by GPC was 99.5%. See Table 1.

Comparative Example 2

The same reactor as the one used in Example 1 was charged with 253 g of tribromoneopentyl alcohol, 1.1 g of anhydrous aluminum chloride, and 800 g of ethylene tetrachloride, and 40.1 g of phosphorus oxychloride was added dropwise over one hour at 100° C. After the mixture was stirred at 100° C. for one hour, the temperature was increased to 120 ° C. over one hour and the reaction was carried out at this temperature for 2 hours. The reaction rate was 96.3%. When this reaction mixture was cooled, crystals separated out to give a slurry. This slurry was washed with 300 ml of 5% HCl 3 times at room temperature and then filtered. One-half of the filter cake was dried in vacuo at 100° C. to provide 117 g of TTBNPP. The yield was 88.5%, the recovery rate was 91.9%, and the purity was 99.4%. See Table 1.

Comparative Example 3

The reaction procedure of Example 4 was repeated except that dichlorobenzene was used as the reaction solvent. The reaction rate was 97.6%. This reaction mixture was cooled to 85° C. and 40 g of water was added. This mixture was stirred at 85° C. for 30 minutes, after which it was cooled to room temperature, whereupon crystals separated out. This crystal crop was filtered and washed with 200 g of methanol. One-half of the filter cake was dried in vacuo at 130° C. to provide 282 g of TTBNPP. The yield was 92.3%, the recovery rate was 94.6%, and the purity was 99.5%.

The methods for determining the reaction rate and purity, the methods for calculating the yield and recovery rate, and the test procedures as used in the examples and comparative examples are described below. See Table 1.

Reaction Rate and Purity

Analyzed by GPC. TOSO G2000HXL+G1000HXL+G1000HXL was used as the column system and elution was carried out with THF at a flow rate of 1 ml/min. The area percentage found with an RI detector was used.

Yield

Assuming that the purity of tribromoneopentyl alcohol was 100%, the percentage of the corrected yield of TTBNPP with respect to the theoretical yield of TTBNPP was calculated. In the examples and comparative examples, one-half of the filter cake was dried and weighed. Therefore, twice the weight found was regarded as the absolute yield. Moreover, the products in the Examples contained residues of the basic magnesium salt used. Therefore, assuming for simplicity of calculation that the whole amount of the salt added was contained in the product, this amount was subtracted from the absolute yield to arrive at the corrected yield. In the comparative examples, the corrected yield is equivalent to the absolute yield.

Recovery Rate

The recovery rate shows how much of the TTBNPP produced by the reaction could be recovered and represents the value found by dividing the yield by the reaction rate.

Qualitative Test for Volatile Acidic Matter in the Filter Cake

A 30 g portion of the filter cake was taken in a test tube and a glycerol-saturated universal pH test paper was inserted into the neck of the tube and fixed in position by loose packing with degreased cotton. The assembly was set in an aluminum block bath at 100° C. and heated for 5 minutes. The acidic matter was detected from the change in color of the pH test paper. The sample which did not show an acid color was indicated by an open circle and the sample which showed an acid color was indicated by a cross. Qualitative test for volatile acidic matter in the product A 30 g portion of the product was taken in a test tube and subjected to the same qualitative test as described for the filter cake. However, the heating temperature of the aluminum block bath was 200° C.

Color on Melting of the Product and the Thermal Discoloration Test

In the qualitative test of the product for volatile acidic matter, the color immediately after melting and the color after 20 minutes were evaluated.

TABLE 1

|  | Example 1 | Example 2 | Example 3 | Example 4 | Comparative Example 1 | Comparative Example 2 | Comparative Example 3 |
|---|---|---|---|---|---|---|---|
| Tribromoneopentyl alcohol (g) | 488 | 488 | 341 | 585 | 488 | 253 | 585 |
| Phosphorus oxychloride (g) | 76.7 | 76.7 | 53.7 | 92.0 | 76.7 | 40.1 | 92.0 |
| Anhydrous aluminum chloride (g) | 1.0 | 1.0 | 0.4 | 1.2 | 1.0 | 1.1 | 1.2 |
| Reaction solvent | Chlorobenzene | Chlorobenzene | Xylene | Chlorobenzene | Chlorobenzene | Ethylene tetrachloride | Dichlorobenzene |
| Amount (g) | 500 | 500 | 600 | 400 | 500 | 800 | 400 |
| Basic magnesium salt | Magnesium hydroxide | Magnesium carbonate | Magnesium hydroxide | Magnesium hydroxide | — | — | — |
| Amount (wt. % of theoretical yield of TTBNPP) | 0.5 | 2.0 | 1.0 | 5.0 | — | — | — |
| Amount (g) | 2.6 | 10.2 | 3.6 | 30.6 | — | — | — |
| Mode of addition | Powder added | Slurry in 100 g of chlorobenzene | Slurry in 10 g of xylene | Slurry in 50 g of chlorobenzene | — | — | — |
| Crystallization | o | o | o | o | x | o | o (after addition of water) |
| Amount of water or hot water added (g) | 200 | 25 | 100 | 200 | — | Washed with 5% HCl | 40 |
| Absolute yield (g) | 482 | 490 | 344 | 626 | 400 | 234 | 564 |
| Percent yield (%) | 94.0 | 94.1 | 95.4 | 97.4 | 78.4 | 88.5 | 92.3 |
| Recovery rate (%) | 96.7 | 96.6 | 98.9 | 99.6 | 80.6 | 91.9 | 94.6 |
| Volatile acidic matter in filter cake | o | o | o | o | x | x | x |
| Product Purity (%) | 99.9 | 99.8 | 99.5 | 99.6 | 99.5 | 99.4 | 99.5 |
| Volatile acidic matter | o | o | o | o | x | x | x |
| Color upon melting | Substantially colorless | Substantially colorless | Substantially colorless | Substantially colorless | Substantially colorless | Substantially colorless | Paint yellow |
| Color after 20 min. | Substantially colorless | Substantially colorless | Substantially colorless | Substantially colorless | Brown | Brown | Light brown |

INDUSTRIAL APPLICABILITY

By the process of the present invention, tris (tribromoneopentyl) phosphate can be produced in high yield and at a high recovery rate through a simplified procedure with high production safety.

Tris(tribromoneopentyl) phosphate as produced by the process of the present invention is of high quality, being free of volatile acidic matter, and can be used as an excellent flame retardant for organic polymers of high molecular weight, which does not cause mold corrosion and is capable of reducing the discoloration of the polymers.

Therefore, the invention represents an industrially useful technology leading to reduced production cost and satisfactory product quality.

What is claimed is:

1. A process for producing tris(tribromoneopentyl) phosphate comprising reacting tribromoneopentyl alcohol with phosphorus oxyhalide in the presence of anhydrous aluminum chloride catalyst in an organic solvent characterized in that a basic magnesium salt is added to the reaction mixture at completion of the reaction.

2. The process according to claim 1 wherein said basic magnesium salt is at least one member selected from the group consisting of magnesium oxide, magnesium hydroxide, magnesium carbonate, magnesium carbonate-magnesiumhydroxide, and their hydrates and is added in a proportion of 0.01–10 weight % relative to the theoretical yield of tris(tribromoneopentyl) phosphate.

3. The process according to claim 2 further characterized in that addition of said basic magnesium salt is carried out at a temperature not causing precipitation of tris (tribromoneopentyl) phosphate from the reaction mixture.

4. The process according to claim 3 further characterized in that water is added to the mixture obtained after addition of the basic magnesium salt.

* * * * *